United States Patent
Stamm et al.

(10) Patent No.: US 10,519,097 B2
(45) Date of Patent: Dec. 31, 2019

(54) PROCESS FOR MAKING MIXTURES OF CHELATING AGENTS

(71) Applicant: BASF SE, Ludwigshafen (DE)

(72) Inventors: Armin Stamm, Nieder-Olm (DE); Thomas Schmidt, Neustadt (DE); Christopher Orr, Houston, TX (US); Jeremy Manning, Ypislanti, MI (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/573,155

(22) PCT Filed: May 3, 2016

(86) PCT No.: PCT/EP2016/059821
§ 371 (c)(1),
(2) Date: Nov. 10, 2017

(87) PCT Pub. No.: WO2016/180664
PCT Pub. Date: Nov. 17, 2016

(65) Prior Publication Data
US 2018/0105486 A1 Apr. 19, 2018

(30) Foreign Application Priority Data

May 13, 2015 (EP) ..................................... 15167630

(51) Int. Cl.
| | | |
|---|---|---|
| *C07C 227/18* | (2006.01) | |
| *C11D 3/33* | (2006.01) | |
| *C01D 1/04* | (2006.01) | |
| *C07C 229/16* | (2006.01) | |
| *C11D 11/00* | (2006.01) | |

(52) U.S. Cl.
CPC .............. *C07C 227/18* (2013.01); *C01D 1/04* (2013.01); *C07C 229/16* (2013.01); *C11D 3/33* (2013.01); *C11D 11/0023* (2013.01)

(58) Field of Classification Search
None
See application file for complete search history.

(56) References Cited

U.S. PATENT DOCUMENTS

| | | | |
|---|---|---|---|
| 4,973,730 A | 11/1990 | Baur et al. | |
| 5,019,296 A | 5/1991 | Baur et al. | |
| 5,786,313 A | 7/1998 | Schneider et al. | |
| 6,005,141 A | 12/1999 | Schneider et al. | |
| 6,008,176 A | 12/1999 | Schneider et al. | |
| 6,494,263 B2 | 12/2002 | Todd | |
| 7,671,234 B2 | 3/2010 | Oftring et al. | |
| 7,754,911 B2 | 7/2010 | Oftring et al. | |
| 2009/0194873 A1 | 8/2009 | Lim | |
| 2010/0222610 A1 | 9/2010 | Boonstra et al. | |
| 2010/0324334 A1 | 12/2010 | Boonstra et al. | |
| 2016/0159730 A1 | 6/2016 | Carstens et al. | |

FOREIGN PATENT DOCUMENTS

| | | |
|---|---|---|
| CN | 102993034 B | 11/2014 |
| DE | 198 19 187 A | 11/1999 |
| DE | 10 2005 021 055 A1 | 11/2006 |
| EP | 0 287 885 A1 | 10/1988 |
| EP | 0 703 971 A | 4/1996 |
| EP | 0 851 023 A | 7/1998 |
| EP | 2 774 913 A1 | 9/2014 |
| JP | 11-92436 A | 4/1999 |
| JP | H1192436 * | 4/1999 |
| WO | 94/29421 | 12/1994 |
| WO | 2009/024519 A1 | 2/2009 |
| WO | WO 2012150155 * | 11/2012 |
| WO | 2015/007630 A1 | 1/2015 |
| WO | 2015/036324 A1 | 3/2015 |

OTHER PUBLICATIONS

English language translation of Kaneko (JPH1192436, published on Apr. 6, 1999, p. 1-43) (Year: 1999).*
Water Hardness, downloaded from https://www.thekrib.com/Plants/CO2/hardness-larryfrank.html on Dec. 19, 2018, p. 1-5 (Year: 2018).*
International Search Report dated Jul. 8, 2016, in PCT/EP2016/059821 filed May 3, 2016.
Extended European Search Report dated Jan. 7, 2016 in Patent Application No. 15167630.1.

* cited by examiner

*Primary Examiner* — Amy C Bonaparte
(74) *Attorney, Agent, or Firm* — Oblon, McClelland, Maier & Neustdt, L.L.P.

(57) ABSTRACT

Process for making a chelating agent according to the general formula (I), $R^1$—$CH(COOX^1)$—$N(CH2COOX^1)_2$ wherein $R^1$ is selected from hydrogen, $C_1$-$C_4$-alkyl, phenyl, benzyl, $CH_2OH$, and $CH_2CH_2COOX^1$, $X^1$ is $(M_xH_{1-x})$, M being selected from alkali metal, x is in the range of from 0.6 to 1, said process comprising the following steps: (a) providing a solid, a slurry or a solution of a compound according to general formula (II a) $R^1$—$CH(COOX^2)$—$N(CH_2CN)_2$ wherein $X^2$ is $(M_yH_{1-y})$, M being selected from alkali metal, y is in the range of from zero to 1, (b) contacting said solid or slurry or solution with an aqueous solution of alkali metal hydroxide, wherein the molar ratio of alkali metal ions to nitrile groups is in the range of from 0.6:1 to 0.95:1, (c) reacting said compound according to general formula (II a) with said alkali metal hydroxide.

13 Claims, No Drawings

PROCESS FOR MAKING MIXTURES OF CHELATING AGENTS

The present invention is directed towards a process for making a chelating agent according to the general formula (I), $$R^1\text{—CH(COOX}^1\text{)—N(CH}_2\text{COOX}^1\text{)}_2 \quad (I)$$

wherein
$R^1$ is selected from hydrogen, $C_1$-$C_4$-alkyl, phenyl, benzyl, $CH_2OH$, and $CH_2CH_2COOX^1$,
$X^1$ is $(M_xH_{1-x})$, M being selected from alkali metal,
x is in the range of from 0.6 to 1,
said process comprising the following steps:
(a) providing a solid, a slurry or a solution of a compound according to general formula (II a)

$$R^1\text{—CH(COOX}^2\text{)—N(CH}_2\text{CN)}_2 \quad (II\ a)$$

wherein
$X^2$ is $(M_yH_{1-y})$, M being selected from alkali metal,
y is in the range of from zero to 1,
(b) contacting said solid or slurry or solution with an aqueous solution of alkali metal hydroxide, wherein the molar ratio of alkali metal ions to nitrile groups is in the range of from 0.6:1 to 0.95:1,
(c) reacting said compound according to general formula (II a) with said alkali metal hydroxide.

Additionally, the present invention is directed towards novel mixtures of chelating agents, and to uses of such mixtures.

Chelating agents such as, but not limited to methyl glycine diacetic acid (MGDA) and their respective alkali metal salts are useful sequestrants for alkaline earth metal ions such as $Ca^{2+}$ and $Mg^{2+}$. For that reason, they are recommended and used for various purposes such as laundry detergents and for automatic dishwashing (ADW) formulations, in particular for so-called phosphate-free laundry detergents and phosphate-free ADW formulations. For shipping such chelating agents, in most cases either solids such as granules are being applied or aqueous solutions.

MGDA and other chelating agents may be made by an alkylation of amino acids with formaldehyde and hydrocyanic acid or an alkali metal cyanide followed by saponification with alkali hydroxide. In order to secure complete saponification a stoichiometric amount of alkali hydroxide or an excess of alkali hydroxide is applied, see, e.g., U.S. Pat. No. 7,671,234. In other methods, MGDA is made by addition of $NH(CH_2CN)_2$ and hydrocyanic acid to acetaldehyde under formation of a trinitrile, followed by hydrolysis, see, e.g., U.S. Pat. No. 7,754,911.

However, stainless steels such as, but not limited to 316 steel types, 321 types and 317 types suffer remarkable corrosion from the reaction conditions if applied in reaction apparatuses for the saponification. Although it is possible to use special steels other than stainless steels it is desirable to find a process that affords chelating agents and that may be performed in apparatuses made from or containing parts made from stainless steel, said parts being exposed to the reaction mixture from the saponification step.

Accordingly, the process defined at the outset has been found, hereinafter also referred to as inventive process or as process according to the (present) invention. The inventive process relates to the manufacturing of a chelating agent according to the general formula (I), $$R^1\text{—CH(COOX}^1\text{)—N(CH}_2\text{COOX}^1\text{)}_2 \quad (I)$$

wherein
$R^1$ is selected from
hydrogen,
$C_1$-$C_4$-alkyl, linear or branched, for example methyl, ethyl, n-propyl, isopropyl, n-butyl, sec.-butyl, isobutyl, and tert.-butyl, preferred are methyl and isopropyl and even more preferred is methyl,
phenyl, benzyl, $CH_2OH$, and $CH_2CH_2COOX^1$,
$X^1$ is $(M_xH_{1-x})$, M being selected from alkali metal, for example lithium, sodium, potassium and mixtures of at least two of the forgoing, preferred are sodium and potassium and mixtures from sodium and potassium and even more preferred is sodium,
x is in the range of from 0.6 to 1, preferred from 0.65 to 0.9, even more preferred 0.7 to 0.9.

In a preferred embodiment of the present invention, $R^1$ is selected from $C_1$-$C_4$-alkyl and $CH_2CH_2COOX^1$, and M is sodium or potassium or combinations thereof. In an even more preferred embodiment, $R^1$ is methyl and M is sodium.

The inventive process comprises steps (a) to (c) as mentioned above. The steps (a) to (c) shall be explained in more detail below.

Step (a) refers to providing a solid or a slurry or a solution of a compound according to general formula (II a)

$$R^1\text{—CH(COOX}^2\text{)—N(CH}_2\text{CN)}_2 \quad (II\ a)$$

including mixtures from each at least one compound according to formula (II a) and one compound according to formula (II b)

$$R^1\text{—CH(CN)—N(CH}_2\text{CN)}_2 \quad (II\ b)$$

preferably a compound of general formula (II a).

Providing a solid means in the context of step (a) of the inventive process that compound according to general formula (II a) is provided as a solid mass.

Said slurry or solution is preferably an aqueous slurry or an aqueous solution, preferably an aqueous solution. Such slurry or solution, respectively, may have a total solids content in the range of from 5 to 60% by weight, preferably 30 to 50% by weight. The term "aqueous" refers to a continuous phase or solvent comprising in the range of from 50 to 100 vol-% of water, preferably 70 to 100 vol-% of water, referring to the total continuous phase or solvent, respectively. Examples of suitable solvents other than water are alcohols such as methanol, ethanol and isopropanol, furthermore diols such as ethylene glycol and triols such as glycerol.

In formulae (II a) and (II b), the variables are defined as follows. $R^1$ is defined as above.

$X^2$ is $(M_yH_{1-y})$, M being selected from alkali metal, for example lithium, sodium, potassium and mixtures of at least two of the forgoing, preferred are sodium and potassium and mixtures from sodium and potassium and even more preferred is sodium,
y is in the range of from zero to 1, preferably 0.7 to 0.9, Compound according to general formula (II a) may be selected from the respective L- and D-enantiomers and combinations thereof, for example the racemic mixture and from mixtures in which the L-enantiomer prevails, for example with 50 to 99.5% L-enantiomer. Preferred are the racemic mixtures and mixtures that contain 95 to 99.5% L-enantiomer.

In a preferred embodiment of the present invention, $R^1$ in general formula (II a) is methyl, and compound (II a) is predominantly the L-enantiomer, the ratio of L to D being in the range of from 95:1 to 100:1.

Compound according to general formula (II b) is preferably the racemic mixture.

Step (b) of the inventive process refers to contacting said slurry or solution with an aqueous solution of alkali metal hydroxide, wherein the molar ratio of alkali metal ions to nitrile groups is in the range of from 0.6:1 to 0.95:1, preferably 0.7 to 0.9.

In one embodiment of the present invention alkali metal hydroxide is selected from hydroxides of lithium, sodium, potassium and combinations of least two of the foregoing. Preferred are sodium hydroxide, potassium hydroxide, mixtures of sodium hydroxide and potassium hydroxide and even more preferred is sodium hydroxide.

Aqueous solutions of alkali metal hydroxide may have a concentration in the range of from 1% by weight to 65% by weight, preferably from 10 to 55% by weight.

Aqueous solutions of alkali metal hydroxide may contain one or more impurities such as, but not limited to alkali metal carbonate. For example, aqueous solutions of sodium hydroxide may contain 0.01 to 1% sodium carbonate.

Said contacting may be performed by charging a reaction vessel with an aqueous solution of alkali metal hydroxide and then adding slurry or solution of compound according to general formula (II a), respectively, in one or more portions. In an alternative embodiment, said contacting may be performed by charging a reaction vessel with a portion of aqueous solution of alkali metal hydroxide and then adding slurry or solution of compound according to general formula (II a), respectively, in one or more portions, and the remaining solution of alkali metal hydroxide, consecutively or preferably in parallel. In an alternative embodiment, said contacting may be performed by continuously combining solution or slurry of compound according to general formula (II a) and aqueous solution of alkali metal hydroxide.

In embodiments in which aqueous solutions of alkali metal hydroxide is added in two portions in step (b), the first portion may contain 10 to 50 mole-% of the required alkali metal hydroxide and the second portion may contain the remaining 50 to 90 mole-%.

In embodiments in which compound according to general formula (II a) is added in two portions in step (b), the first portion may contain 10 to 50 mole-% of the required compound according to general formula (II a) and the second portion may contain the remaining 50 to 90 mole-%.

Step (b) of the inventive process may be performed at a temperature in the range of from zero to 80° C., preferably 5 to 75° C. and sometimes up to 50° C. and even more preferably from 25 to 40° C. A very particular temperature range is from 35 to 70° C. In embodiments wherein aqueous solution of alkali metal hydroxide or slurry or solution of compound according to general formula (II a) are combined in two or more portions said portions may be combined at the same or at different temperatures.

Step (b) of the inventive process may have a duration of 30 minutes to 24 hours, preferably 1 to 12 hours, even more preferably 2 to 6 hours.

Step (b) of the inventive process may be performed under a pressure in the range of from 0.5 to 10 bar, preferably normal pressure.

In one embodiment of the present invention, the reaction vessel in which step (b) is performed contains at least one part made from stainless steel or stainless steel that is exposed to the mixture formed in step (b).

Step (c) of the inventive process refers to reacting said compound according to general formula (II a) with said alkali metal hydroxide.

Step (c) of the inventive process may be performed at a temperature in the range of from 30 to 200° C., preferably 70 to 190° C.

Step (c) of the inventive process may be performed at one temperature. In preferred embodiments, however, step (c) is performed in the form of two or more sub-steps (c1), (c2) and optionally more, of which the sub-steps are performed at different temperatures. Preferably, each sub-step may be performed at a temperature that is higher than the temperature at which the previous sub-step was performed. In the context of the present invention, sub-steps differ in temperature by at least 10° C., said temperature referring to the average temperature. In a preferred embodiment of the present invention, step (c) comprises at least two sub-steps (c1) and (c2), sub-step (c2) being performed at a temperature at least 20° C. higher than sub-step (c1), preferably at least 25° C. In a preferred embodiment, step (c) comprises at least two sub-steps (c1) and (c2), sub-step (c2) being performed at a temperature from 20° C. to 150° C. higher than sub-step (c1).

Preferably, a sub-step is performed over a period of at least 30 minutes. Even more preferably, a sub-step is performed over a period of 30 minutes to 5 hours, preferably up to 2 hours.

In one embodiment of the present invention, step (c) has an overall duration in the range of from 30 minutes up to 24 hours, preferably 2 to 16 hours.

In one embodiment of the present invention, at least one sub-step of step (c) is carried out at a temperature in the range of from 50 to 90° C., preferably 70 to 80° C.

In one embodiment of the present invention, at least one sub-step of step (c) is carried out at a temperature in the range of from 90 to 200° C., preferably 150 to 190° C.

In one embodiment of the present invention, at least one sub-step of step (c) is carried out at a temperature in the range of from 40 to 60° C., another sub-step of step (c) is carried out at a temperature in the range of from 50 to 80° C., and at least another sub-step of step (c) is carried out at a temperature in the range of from 100 to 200° C.

In one embodiment of the present invention, ammonia formed during the reaction is removed, continuously or discontinuously, for example by stripping or by distilling it off, for example at a temperature of at least 90° C., preferably 90 to 105° C.

In one embodiment of the present invention, water is added during the course of step (c), for example in order to compensate for the loss of water due to ammonia removal.

In one embodiment of the present invention, step (c) is carried out at normal pressure or at a pressure above 1 bar, for example 1.1 to 40 bar, preferably 5 to 25 bar. In embodiments with two or more sub-steps of step (c), subsequent sub-steps are preferably carried out at a pressure at least as high as the previous sub-step.

Step (c) may be carried out in a stirred tank reactor, or in a plug flow reactor, or in a cascade of at least two stirred tank reactors, for example 2 to 6 stirred tank reactors, or in a combination of a cascade of 2 to 6 stirred tank reactors with a plug flow reactor.

Especially in embodiments wherein the final sub-step of step (c) is carried out in a plug flow reactor, said final sub-step may be carried out at elevated pressure such as 1.5 to 40 bar, preferably at least 20 bar. The elevated pressure may be accomplished with the help of a pump or by autogenic pressure elevation.

In one embodiment of the present invention, the reaction vessel in which step (c) is performed contains at least one part made from stainless steel that is exposed to the reaction mixture according to step (c).

In one embodiment of the present invention, at least one reaction vessel in which a sub-step of step (c) is performed contains at least one part made from stainless steel that is exposed to the reaction mixture according to step (c).

During step (c), a partial or complete racemization may take place if compound according to general formula (II a) is optically active and if step (c) or at least one sub-step of step (c) is carried at a sufficiently high temperature. Without wishing to be bound by any theory, it is likely that racemization takes place on the stage of the above L-monoamide or L-diamide or of the L-isomer of compound according to formula (I).

In one embodiment of the present invention, the inventive process may comprise additional steps other than steps (a), (b) and (c) disclosed above. Such additional steps may be, for example, one or more decolourization steps, for example treatment with activated carbon or with peroxide such as $H_2O_2$ or by irradiation with UV-light in the absence or presence of $H_2O_2$.

A further step other than step (a), (b) or (c) that may be carried out after step (c) is stripping with air or nitrogen or steam in order to remove ammonia. Said stripping can be carried out at temperatures in the range of from 90 to 110° C. By nitrogen or air stripping, water can be removed from the solution so obtained. Stripping is preferably carried out at a pressure below normal pressure, such as 650 to 950 mbar.

In embodiments wherein an inventive solution is desired, the solution obtained from step (c) is just cooled down and, optionally, concentrated by partially removing the water. If dry samples of inventive mixtures are required, the water can be removed by spray drying or spray granulation.

The inventive process may be carried out as a batch process, or as a semi-continuous or continuous process.

By performing the inventive process, a chelating agent of general formula (I) is obtained. Said chelating agent is not obtained in pure form but it contains certain amounts of at least one mono- or diamide according to general formula (III a) and (III b):

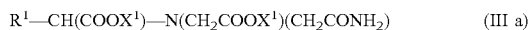  (III a)

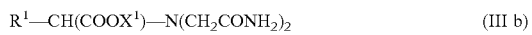  (III b)

wherein the variables $R^1$ and $X^1$ are as defined above. The chelating power of mixtures obtained according to the inventive process is excellent. While performing the inventive process, stainless steel reaction vessels and especially stainless steel parts of reaction vessels exposed to the reaction mixture suffer less wear-off or corrosion than in process in which an excess of alkali metal hydroxide is employed.

Preferably, such complexing agent according to general formula (I) contains only very low amounts of inorganic basic salts, for example in total 1 ppm to 1.5% by weight of inorganic non-basic salt, based on the respective mixture of compounds according to general formulae (I) and (III a) and (III b). In the context of the present invention, basic inorganic salts may also be referred to as alkaline inorganic salts.

The chelating power, hereinafter also referred to as complexing power, of such mixtures may be determined by titration with aqueous solutions of Fe(+III) salt solution, for example of aqueous solutions of $FeCl_3$.aq. Values of complexing power with respect to alkali earth metals are excellent as well.

Another aspect of the present invention refers to mixtures of compounds that comprise (A) at least one compound according to general formula (I)

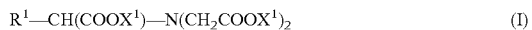  (I)

(B) at least one compound selected from compounds according to general formula (III a) and (III b):

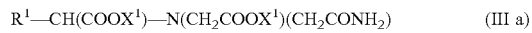  (III a)

  (III b)

wherein
$R^1$ is selected from
hydrogen,
$C_1$-$C_4$-alkyl, linear or branched, for example methyl, ethyl, n-propyl, isopropyl, n-butyl, sec.-butyl, isobutyl, and tert.-butyl, preferred are methyl and isobutyl and even more preferred is methyl,
phenyl, benzyl, $CH_2OH$, and $CH_2CH_2COOX^1$,
$X^1$ is $(Na_xH_{1-x})$,
x is in the range of from 0.6 to 1,
component (A) and component (B) being in a molar ratio in the range of from 2.5:1 to 0.1:1, preferably from 2.0:1 to 0.25 to 1,
and in total 1 ppm to 1.5% by weight of inorganic non-basic salt, based on the respective inventive mixture.

In a preferred embodiment of the present invention, $R^1$ is methyl.

In the context of the present invention, the above mixtures may also be referred to as inventive mixtures or mixtures according to the present invention.

The components of inventive mixtures will be explained in more detail below.

Component (A) may be a racemic mixture or a pure enantiomer, for example the L-enantiomer, or a mixture of L- and D-enantiomers in which one of the enantiomers prevails, preferably the L-enantiomer prevails. In a preferred embodiment of the present invention component (A) is a mixture of enantiomers containing predominantly the respective L-enantiomer with an enantiomeric excess (ee) in the range of from 10 to 98%.

In an even more preferred embodiment of the present invention component (A) is a mixture of enantiomers containing predominantly the respective L-enantiomer with an enantiomeric excess (ee) in the range of from 10 to 98%, and $R^1$ is methyl.

In one embodiment of the present invention, the enantiomeric excess of the respective L-isomer of component (A) is in the range of from 10 to 98%, preferably in the range of from 12.5 to 85% and even more preferred up to 75%. In other embodiments, all components of inventive mixtures constitute the respective racemic mixtures.

In embodiments where component (A) comprises two or more compounds, the ee refers to the enantiomeric excess of all L-isomers present in component (A) compared to all D-isomers in component (A). For example, in cases wherein a mixture of the di- and trisodium salt of MGDA is present, the ee refers to the sum of the disodium salt and trisodium salt of L-MGDA with respect to the sum of the disodium salt and the trisodium salt of D-MGDA.

The enantiomeric excess can be determined by measuring the polarization (polarimetry) or preferably by chromatography, for example by HPLC with a chiral column, for example with one or more cyclodextrins as immobilized phase. Preferred is determination of the ee by HPLC with an immobilized optically active ammonium salt such as D-penicillamine.

Component (B) is a mono- or diamide or a mixture therefrom. Component (B) comprises a mixture of compounds according to general formula (III a) and (III b).

In embodiments wherein some compound (II b) has been used as starting material, the inventive mixture may contain some compound that has the general formula

$$R^1\text{—CH(CONH}_2)\text{—N(CH}_2\text{COOX}^1)_2 \quad \text{(III c)}$$

Component (B) may be present as racemic mixture or in the form of a mixture of enantiomers in which the L-enantiomer predominates, for example with an enantiomeric excess in the range of from 5 to 95%, more preferably 15 to 90%. Compound according to general formula (III c)—if applicable—is usually present as racemic mixture.

In one embodiment of the present invention, inventive mixtures may contain in the range of from 0.1 to 10% by weight of one or more optically inactive impurities, at least one of the impurities being at least one of the impurities being selected from iminodiacetic acid, racemic N-carboxymethyl-alanine, formic acid, glycolic acid, propionic acid, acetic acid and their respective alkali metal or mono-, di- or triammonium salts.

In one aspect of the present invention, inventive mixtures may contain less than 0.2% by weight of nitrilotriacetic acid (NTA), preferably 0.01 to 0.1% by weight.

In one embodiment of the present invention, inventive mixtures in which $R^1$ is methyl may additionally contain 0.1 to 3% by weight with respect to the sum of (A) and (B), of at least one diacetic acid derivative of glutamic acid, of aspartate, or of valine, or 0.1 to 3% by weight of the tetraacetic acid derivative of lysine, or 0.1 to 3% by weight of the mono-acetate of proline.

In one embodiment of the present invention, inventive mixtures that contain an optically active compound according to general formula (I) may contain one or more optically active impurities. Examples of optically active impurities are L-carboxymethylalanine and its respective mono- or dialkali metal salts, and optically active mono- or diamides that result from an incomplete saponification of the dinitriles, see below. A further example of an optically active impurity is the respective mono-carboxymethyl derivative of (B). Preferably, the amount of optically active impurities is in the range of from 0.01 to 2% by weight, referring to the inventive mixture solution. Even more preferred, the amount of optically active impurities is in the range of from 0.1 to 0.2% by weight.

In one aspect of the present invention, inventive mixtures may contain minor amounts of cations other than alkali metal. It is thus possible that minor amounts, such as 0.01 to 5 mol-% of total inventive mixture, based on anion, bear ammonium cations or alkali earth metal cations such as $Mg^{2+}$ or $Ca^{2+}$, or transition metal ions such as $Fe^{2+}$ or $Fe^{3+}$ cations.

Inventive mixtures display a very good solubility, especially in water and aqueous alkali metal hydroxide solutions. Such very good solubility can be seen, e.g., in a temperature range of from zero ° C. to 40° C., in particular at room temperature and/or at zero and/or +10° C.

Inventive mixtures also display a very good chelating power. The chelating power of inventive mixtures may be determined by titration with aqueous solutions of Fe(+III) salt solution, for example of aqueous solutions of $FeCl_3$.aq.

Another aspect of the present invention is an aqueous solution of an inventive mixture, hereinafter also referred to as inventive solution or as inventive aqueous solution. Preferably, inventive aqueous solutions contain in the range of from 30 to 70% by weight of said inventive mixture, preferably 40 to 65% by weight, even more preferably 48 to 60% by weight. Such aqueous solutions are hereinafter also being referred to as inventive solutions or solutions according to the present invention. Inventive solutions do not show amounts of precipitation or crystallization on addition of seed crystals or mechanical stress at ambient temperature. Inventive solutions do not exhibit any visible turbidity.

In a preferred embodiment of the present invention, inventive solutions do not contain major amounts of alkali metal of mono- and dicarboxylic acids such as acetic acid, propionic acid, maleic acid, acrylic acid, adipic acid, succinic acid, and the like. Major amounts in this context refer to amounts over 0.5% by weight.

In one embodiment of the present invention, inventive solutions have a pH value in the range of from 8 to 14, preferably 10.0 to 13.5, even more preferably 10 to 12.

Inventive mixtures as well as inventive solutions may contain one or more inorganic non-basic salts such as—but not limited to—alkali metal halide or preferably alkali metal sulphate, especially potassium sulphate or even more preferably sodium sulphate. The content of inorganic non-basic salt may be in the range of from 1 ppm or more up to 1.5% by weight, referring to the respective inventive mixture or the solids content of the respective inventive solution. Even more preferably, inventive mixtures as well as inventive solutions do not contain significant amounts of inorganic non-basic salt, for example in the range of from 50 ppm to 0.05% by weight, referring to the respective inventive mixture or the solids content of the respective inventive solution. Even more preferably inventive mixtures contain 1 to 50 ppm by weight of sum of chloride and sulphate, referring to the respective inventive mixture. The contents of sulphate may be determined, for example, by gravimetric analysis or by ion chromatography.

Furthermore, inventive mixtures as well as inventive solutions exhibit advantageous olfactory behaviour as well as a very low tendency to colorize such as yellowing upon storage.

Another aspect of the present invention is directed towards the use of inventive mixtures for removal of alkali earth metal cations and/or iron cations from water. The term removal as used in this context refers to the chelating—or complexing—of alkali earth metal cations and/or iron cations so they do not form precipitates with anions that are present in certain applications and that may lead to undesired precipitates. For example, in laundry detergent applications or automatic dishwashing applications, carbonate ions may lead to the precipitation of calcium carbonate and magnesium carbonate that lead to undesired deterioration of the laundry detergent—or automatic dishwashing detergent, as the case may be—in particulate with respect to spotting.

A further aspect of the present invention is the use of an inventive mixture or an inventive solution for the manufacture of laundry detergent compositions and of detergent compositions for cleaners. A further aspect is a process for manufacture of laundry detergents and of detergent compositions cleaners by using an inventive mixture or an inventive solution. Depending on whether a mixing in aqueous formulation or in dry matter is desired, and depending on whether a liquid or solid detergent composition is desired, an inventive aqueous solution or an inventive mixture of isomers can be used. Mixing can be performed by formulation steps known per se.

In particular when mixing is being carried out with an inventive solution for the production of a solid laundry detergent compositions or a solid detergent composition for cleaners, such use is advantageous because it allows to add only reduced amounts of water to be removed later, and it allows for great flexibility because no additional ingredients such as polymer, surfactants or salts are present that otherwise reduce flexibility of the detergent manufacturer.

In one embodiment of the present invention, inventive aqueous solutions may be used as such for the manufacture of laundry detergent compositions or for detergent compositions for cleaners. In other embodiments, inventive aqueous solutions may be used in fully or preferably partially neutralized form for the manufacture of laundry detergent compositions or for detergent compositions for cleaners. In one embodiment, inventive aqueous solutions may be used in fully or preferably partially neutralized form for the manufacture of laundry detergent compositions or of detergent compositions for cleaners, said neutralization being performed with an inorganic acid (mineral acid). Preferred inorganic acids are selected from $H_2SO_4$, HCl, and $H_3PO_4$. In other embodiments, inventive aqueous solutions may be used in fully or preferably partially neutralized form for the manufacture of laundry detergent compositions or of detergent compositions for cleaners, said neutralization being performed with an organic acid. Preferred organic acids are selected from $CH_3SO_3H$, acetic acid, propionic acid, and citric acid.

In the context of the present invention, the term "detergent composition for cleaners" includes cleaners for home care and for industrial or institutional applications. The term "detergent composition for cleaners" includes compositions for dishwashing, especially hand dishwash and automatic dishwashing and ware-washing, and compositions for hard surface cleaning such as, but not limited to compositions for bathroom cleaning, kitchen cleaning, floor cleaning, descaling of pipes, window cleaning, car cleaning including truck cleaning, furthermore, open plant cleaning, cleaning-in-place, metal cleaning, disinfectant cleaning, farm cleaning, high pressure cleaning, but not laundry detergent compositions.

In the context of the present invention and unless expressly stated otherwise, percentages in the context of ingredients of laundry detergent compositions are percentages by weight and refer to the total solids content of the respective laundry detergent composition. In the context of the present invention and unless expressly stated otherwise, percentages in the context of ingredients of detergent composition for cleaners are percentages by weight and refer to the total solids content of the detergent composition for cleaner.

In one embodiment of the present invention, laundry detergent compositions according to the present invention may contain in the range of from 1 to 30% by weight of inventive mixture. Percentages refer to the total solids content of the respective laundry detergent composition.

In one embodiment of the present invention, detergent compositions for cleaners according to the present invention may contain in the range of from 1 to 50% by weight of inventive mixture, preferably 5 to 40% by weight and even more preferably 10 to 25% by weight. Percentages refer to the total solids content of the respective detergent composition for home care.

Particularly advantageous laundry detergent compositions and of detergent compositions for cleaners, especially for home care may contain one or more chelating agent other than mixtures according to the present invention. Advantageous detergent compositions for cleaners and advantageous laundry detergent compositions may contain one or more mixture (in the context of the present invention also referred to as sequestrant) other than a mixture according to the present invention. Examples for sequestrants other than the chelating agents according to the present invention are IDS (iminodisuccinate), citrate, phosphonic acid derivatives, for example the disodium salt of hydroxyethane-1,1-diphosphonic acid ("HEDP"), and polymers with complexing groups like, for example, polyethylenimine in which 20 to 90 mole-% of the N-atoms bear at least one $CH_2COO^-$ group, and their respective alkali metal salts, especially their sodium salts, IDS-$Na_4$, and trisodium citrate, and phosphates such as STPP (sodium tripolyphosphate). Due to the fact that phosphates raise environmental concerns it is preferred that advantageous detergent compositions for cleaners and advantageous laundry detergent compositions are free from phosphate. "Free from phosphate" should be understood in the context of the present invention, as meaning that the content of phosphate and polyphosphate is in sum in the range from 10 ppm to 0.2% by weight, determined by gravimetry.

Advantageous detergent compositions for cleaners and advantageous laundry detergent compositions may contain one or more surfactant, preferably one or more non-ionic surfactant.

Preferred non-ionic surfactants are alkoxylated alcohols, di- and multiblock copolymers of ethylene oxide and propylene oxide and reaction products of sorbitan with ethylene oxide or propylene oxide, alkyl polyglycosides (APG), hydroxyalkyl mixed ethers and amine oxides.

Preferred examples of alkoxylated alcohols and alkoxylated fatty alcohols are, for example, compounds of the general formula (IV)

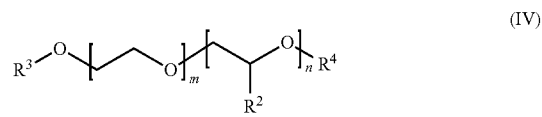

(IV)

in which the variables are defined as follows:
$R^2$ is identical or different and selected from hydrogen and linear $C_1$-$C_{10}$-alkyl, preferably in each case identical and ethyl and particularly preferably hydrogen or methyl,
$R^3$ is selected from $C_8$-$C_{22}$-alkyl, branched or linear, for example n-$C_8H_{17}$, n-$C_{10}H_{21}$, n-$C_{12}H_{25}$, n-$C_{14}H_{29}$, n-$C_{16}H_{33}$ or n-$C_{18}H_{37}$,
$R^4$ is selected from C1-$C_{10}$-alkyl, methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, n-octyl, 2-ethylhexyl, n-nonyl, n-decyl or isodecyl,
m and n are in the range from zero to 300, where the sum of n and m is at least one, preferably in the range of from 3 to 50. Preferably, m is in the range from 1 to 100 and n is in the range from 0 to 30.

In one embodiment, compounds of the general formula (III) may be block copolymers or random copolymers, preference being given to block copolymers.

Other preferred examples of alkoxylated alcohols are, for example, compounds of the general formula (V)

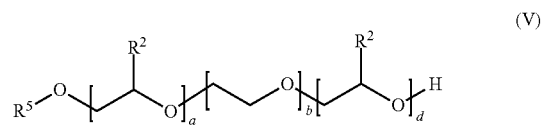

(V)

wherein
R² is identical or different and selected from hydrogen and linear $C_1$-$C_{10}$-alkyl, preferably identical in each case and ethyl and particularly preferably hydrogen or methyl,
R⁵ is selected from $C_6$-$C_{20}$-alkyl, branched or linear, in particular n-$C_8H_{17}$, n-$C_{10}H_{21}$, n-$C_{12}H_{25}$, n-$C_{13}H_{27}$, n-$C_{15}H_{31}$, n-$C_{14}H_{29}$, n-$C_{16}H_{33}$, n-$C_{18}H_{37}$,
a is a number in the range from zero to 10, preferably from 1 to 6,
b is a number in the range from 1 to 80, preferably from 4 to 20,
d is a number in the range from zero to 50, preferably 4 to 25.

The sum a+b+d is preferably in the range of from 5 to 100, even more preferably in the range of from 9 to 50.

Preferred examples for hydroxyalkyl mixed ethers are compounds of the general formula (VI)

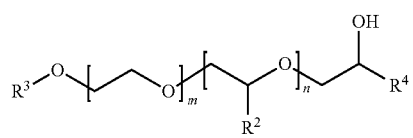

(VI)

in which the variables are defined as follows:
R² is identical or different and selected from hydrogen and linear $C1$-$C_{10}$-alkyl, preferably in each case identical and ethyl and particularly preferably hydrogen or methyl,
R³ is selected from $C_8$-$C_{22}$-alkyl, branched or linear, for example iso-$C_{11}H_{23}$, iso-$C_{13}H_{27}$, n-$C_8H_{17}$, n-$C_{10}H_{21}$, n-$C_{12}H_{25}$, n-$C_{14}H_{29}$, n-$C_{16}H_{33}$ or n-$C_{18}H_{37}$,
R⁴ is selected from $C_1$-$C_{18}$-alkyl, methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, n-octyl, 2-ethylhexyl, n-nonyl, n-decyl, isodecyl, n-dodecyl, n-tetradecyl, n-hexadecyl, and n-octadecyl.

The integers m and n are in the range from zero to 300, where the sum of n and m is at least one, preferably in the range of from 5 to 50. Preferably, m is in the range from 1 to 100 and n is in the range from 0 to 30.

Compounds of the general formulae (IV), (V) and (VI) may be block copolymers or random copolymers, preference being given to block copolymers.

Further suitable nonionic surfactants are selected from di- and multiblock copolymers, composed of ethylene oxide and propylene oxide. Further suitable nonionic surfactants are selected from ethoxylated or propoxylated sorbitan esters. Amine oxides or alkyl polyglycosides, especially linear $C_4$-$C_{16}$-alkyl polyglucosides and branched $C_8$-$C_{14}$-alkyl polyglycosides such as compounds of general average formula (VII) are likewise suitable

(VII)

wherein:
R⁶ is $C_1$-$C_4$-alkyl, in particular ethyl, n-propyl or isopropyl,
R⁷ is —$(CH_2)_2$—R⁶,
G¹ is selected from monosaccharides with 4 to 6 carbon atoms, especially from glucose and xylose,
z in the range of from 1.1 to 4, z being an average number.

Further examples of non-ionic surfactants are compounds of general formula (VIII) and (IX)

(VIII)

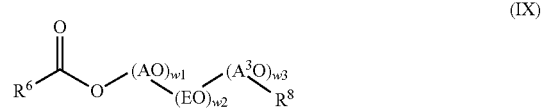

(IX)

AO is selected from ethylene oxide, propylene oxide and butylene oxide,
EO is ethylene oxide, $CH_2CH_2$—O,
R⁸ selected from $C_8$-$C_{18}$-alkyl, branched or linear, and R⁶ is defined as above
A³O is selected from propylene oxide and butylene oxide,
w is a number in the range of from 15 to 70, preferably 30 to 50,
w1 and w3 are numbers in the range of from 1 to 5, and
w2 is a number in the range of from 13 to 35.

An overview of suitable further nonionic surfactants can be found in EP-A 0 851 023 and in DEA 198 19 187.

Mixtures of two or more different nonionic surfactants may also be present.

Other surfactants that may be present are selected from amphoteric (zwitterionic) surfactants and anionic surfactants and mixtures thereof.

Examples of amphoteric surfactants are those that bear a positive and a negative charge in the same molecule under use conditions. Preferred examples of amphoteric surfactants are so-called betaine-surfactants. Many examples of betaine-surfactants bear one quaternized nitrogen atom and one carboxylic acid group per molecule. A particularly preferred example of amphoteric surfactants is cocamidopropyl betaine (lauramidopropyl betaine).

Examples of amine oxide surfactants are compounds of the general formula (X)

(X)

wherein R⁹, R¹⁰, and R¹¹ and are selected independently from each other from aliphatic, cycloaliphatic or $C_2$-$C_4$-alkylene $C_{10}$-$C_{20}$-alkylamido moieties. Preferably, R¹⁰ is selected from $C_8$-$C_{20}$-alkyl or $C_2$-$C_4$-alkylene $C_{10}$-$C_{20}$-alkylamido and R¹¹ and R⁹ are both methyl.

A particularly preferred example is lauryl dimethyl aminoxide, sometimes also called lauramine oxide. A further particularly preferred example is cocamidylpropyl dimethylaminoxide, sometimes also called cocamidopropylamine oxide.

Examples of suitable anionic surfactants are alkali metal and ammonium salts of $C_8$-$C_{18}$-alkyl sulfates, of $C_8$-$C_{18}$-fatty alcohol polyether sulfates, of sulfuric acid half-esters of ethoxylated $C_4$-$C_{12}$-alkylphenols (ethoxylation: 1 to 50 mol of ethylene oxide/mol), $C_{12}$-$C_{18}$ sulfo fatty acid alkyl esters, for example of $C_{12}$-$C_{18}$ sulfo fatty acid methyl esters, furthermore of $C_{12}$-$C_{18}$-alkylsulfonic acids and of $C_{10}$-$C_{18}$-alkylarylsulfonic acids. Preference is given to the alkali metal salts of the aforementioned compounds, particularly preferably the sodium salts.

Further examples for suitable anionic surfactants are soaps, for example the sodium or potassium salts of stearoic acid, oleic acid, palmitic acid, ether carboxylates, and alkylether phosphates.

Preferably, laundry detergent compositions contain at least one anionic surfactant.

In one embodiment of the present invention, laundry detergent compositions may contain 0.1 to 60% by weight of at least one surfactant, selected from anionic surfactants, amphoteric surfactants and amine oxide surfactants.

In one embodiment of the present invention, detergent compositions for cleaners may contain 0.1 to 60% by weight of at least one surfactant, selected from anionic surfactants, amphoteric surfactants and amine oxide surfactants.

In a preferred embodiment, detergent compositions for cleaners and especially those for automatic dishwashing do not contain any anionic surfactant.

Detergent compositions for cleaners and laundry detergent compositions may contain at least one bleaching agent, also referred to as bleach. Bleaching agents may be selected from chlorine bleach and peroxide bleach, and peroxide bleach may be selected from inorganic peroxide bleach and organic peroxide bleach. Preferred are inorganic peroxide bleaches, selected from alkali metal percarbonate, alkali metal perborate and alkali metal persulfate.

Examples of organic peroxide bleaches are organic percarboxylic acids, especially organic percarboxylic acids.

Suitable chlorine-containing bleaches are, for example, 1,3-dichloro-5,5-dimethylhydantoin, N-chlorosulfamide, chloramine T, chloramine B, sodium hypochlorite, calcium hypochlorite, magnesium hypochlorite, potassium hypochlorite, potassium dichloroisocyanurate and sodium dichloroisocyanurate.

Detergent compositions for cleaners and laundry detergent compositions may comprise, for example, in the range from 3 to 10% by weight of chlorine-containing bleach.

Detergent compositions for cleaners and laundry detergent compositions may comprise one or more bleach catalysts. Bleach catalysts can be selected from bleach-boosting transition metal salts or transition metal complexes such as, for example, manganese-, iron-, cobalt-, rutheniumor molybdenum-salen complexes or carbonyl complexes. Manganese, iron, cobalt, ruthenium, molybdenum, titanium, vanadium and copper complexes with nitrogen-containing tripod ligands and also cobalt-, iron-, copper- and ruthenium-amine complexes can also be used as bleach catalysts.

Detergent compositions for cleaners and laundry detergent compositions may comprise one or more bleach activators, for example N-methylmorpholinium-acetonitrile salts ("MMA salts"), trimethylammonium acetonitrile salts, N-acylimides such as, for example, N-nonanoylsuccinimide, 1,5-diacetyl-2,2-dioxohexahydro-1,3,5-triazine ("DADHT") or nitrile quats (trimethylammonium acetonitrile salts).

Further examples of suitable bleach activators are tetraacetylethylenediamine (TAED) and tetraacetylhexylenediamine.

Detergent compositions for cleaners and laundry detergent compositions may comprise one or more corrosion inhibitors. In the present case, this is to be understood as including those compounds which inhibit the corrosion of metal. Examples of suitable corrosion inhibitors are triazoles, in particular benzotriazoles, bisbenzotriazoles, aminotriazoles, alkylaminotriazoles, also phenol derivatives such as, for example, hydroquinone, pyrocatechol, hydroxyhydroquinone, gallic acid, phloroglucinol or pyrogallol.

In one embodiment of the present invention, detergent compositions for cleaners and laundry detergent compositions comprise in total in the range from 0.1 to 1.5% by weight of corrosion inhibitor.

Detergent compositions for cleaners and laundry detergent compositions may comprise one or more builders, selected from organic and inorganic builders. Examples of suitable inorganic builders are sodium sulfate or sodium carbonate or silicates, in particular sodium disilicate and sodium metasilicate, zeolites, sheet silicates, in particular those of the formula $\alpha\text{-}Na_2Si_2O_5$, $\beta\text{-}Na_2Si_2O_5$, and $\delta\text{-}Na_2Si_2O_5$, also fatty acid sulfonates, $\alpha$-hydroxypropionic acid, alkali metal malonates, fatty acid sulfonates, alkyl and alkenyl disuccinates, tartaric acid diacetate, tartaric acid monoacetate, oxidized starch, and polymeric builders, for example polycarboxylates and polyaspartic acid.

Examples of organic builders are especially polymers and copolymers. In one embodiment of the present invention, organic builders are selected from polycarboxylates, for example alkali metal salts of (meth)acrylic acid homopolymers or (meth)acrylic acid copolymers.

Suitable comonomers are monoethylenically unsaturated dicarboxylic acids such as maleic acid, fumaric acid, maleic anhydride, itaconic acid and citraconic acid. A suitable polymer is in particular polyacrylic acid, which preferably has an average molecular weight $M_w$ in the range from 2000 to 40 000 g/mol, preferably 2000 to 10 000 g/mol, in particular 3000 to 8000 g/mol. Also of suitability are copolymeric polycarboxylates, in particular those of acrylic acid with methacrylic acid and of acrylic acid or methacrylic acid with maleic acid and/or fumaric acid, and in the same range of molecular weight.

It is also possible to use copolymers of at least one monomer from the group consisting of monoethylenically unsaturated $C_3\text{-}C_{10}$-mono- or $C_4\text{-}C_{10}$-dicarboxylic acids or anhydrides thereof, such as maleic acid, maleic anhydride, acrylic acid, methacrylic acid, fumaric acid, itaconic acid and citraconic acid, with at least one hydrophilic or hydrophobic monomer as listed below.

Suitable hydrophobic monomers are, for example, isobutene, diisobutene, butene, pentene, hexene and styrene, olefins with 10 or more carbon atoms or mixtures thereof, such as, for example, 1-decene, 1-dodecene, 1-tetradecene, 1-hexadecene, 1-octadecene, 1-eicosene, 1-docosene, 1-tetracosene and 1-hexacosene, $C_{22}$-$\alpha$-olefin, a mixture of $C_{20}$-$C_{24}$-$\alpha$-olefins and polyisobutene having on average 12 to 100 carbon atoms per molecule.

Suitable hydrophilic monomers are monomers with sulfonate or phosphonate groups, and also nonionic monomers with hydroxyl function or alkylene oxide groups. By way of example, mention may be made of: allyl alcohol, isoprenol, methoxypolyethylene glycol (meth)acrylate, methoxypolypropylene glycol (meth)acrylate, methoxypolybutylene glycol (meth)acrylate, methoxypoly(propylene oxide-co-ethylene oxide) (meth)acrylate, ethoxypolyethylene glycol (meth)acrylate, ethoxypolypropylene glycol (meth)acrylate, ethoxypolybutylene glycol (meth)acrylate and ethoxypoly(propylene oxide-co-ethylene oxide) (meth)acrylate. Polyalkylene glycols here may comprise 3 to 50, in particular 5 to 40 and especially 10 to 30 alkylene oxide units per molecule.

Particularly preferred sulfonic-acid-group-containing monomers here are 1-acrylamido-1-propanesulfonic acid, 2-acrylamido-2-propanesulfonic acid, 2-acrylamido-2-methylpropanesulfonic acid, 2-methacrylamido-2-methylpropanesulfonic acid, 3-methacrylamido-2-hydroxypropanesulfonic acid, allylsulfonic acid, methallylsulfonic acid, allyloxybenzenesulfonic acid, methallyloxybenzenesulfonic acid, 2-hydroxy-3-(2-propenyloxy)propanesulfonic acid, 2-methyl-2-propene-1-sulfonic acid, styrenesulfonic acid, vinylsulfonic acid, 3-sulfopropyl acrylate, 2-sulfoethyl methacrylate, 3-sulfopropyl methacrylate, sulfomethacrylamide, sulfomethylmethacrylamide, and salts of said acids, such as sodium, potassium or ammonium salts thereof.

Particularly preferred phosphonate-group-containing monomers are vinylphosphonic acid and its salts.

Moreover, amphoteric polymers can also be used as builders.

Detergent compositions for cleaners and laundry detergent compositions according to the invention may comprise, for example, in the range from in total 10 to 70% by weight, preferably up to 50% by weight, of builder. In the context of the present invention, MGDA is not counted as builder.

In one embodiment of the present invention, detergent compositions for cleaners and laundry detergent compositions according to the invention may comprise one or more cobuilders.

Detergent compositions for cleaners and laundry detergent compositions may comprise one or more antifoams, selected for example from silicone oils and paraffin oils.

In one embodiment of the present invention, detergent compositions for cleaners and laundry detergent compositions comprise in total in the range from 0.05 to 0.5% by weight of antifoam.

Detergent compositions for cleaners and laundry detergent according to the invention may comprise one or more enzymes. Examples of enzymes are lipases, hydrolases, amylases, proteases, cellulases, esterases, pectinases, lactases and peroxidases.

In one embodiment of the present invention, detergent compositions for cleaners and laundry detergent compositions according to the present invention may comprise, for example, up to 5% by weight of enzyme, preference being given to 0.1 to 3% by weight. Said enzyme may be stabilized, for example with the sodium salt of at least one $C_1$-$C_3$-carboxylic acid or $C_4$-$C_{10}$-dicarboxylic acid. Preferred are formates, acetates, adipates, and succinates.

In one embodiment of the present invention, detergent compositions for cleaners and laundry detergent compositions according to the invention comprise at least one zinc salt. Zinc salts can be selected from water-soluble and water-insoluble zinc salts. In this connection, within the context of the present invention, water-insoluble is used to refer to those zinc salts which, in distilled water at 25° C., have a solubility of 0.1 g/l or less. Zinc salts which have a higher solubility in water are accordingly referred to within the context of the present invention as water-soluble zinc salts.

In one embodiment of the present invention, zinc salt is selected from zinc benzoate, zinc gluconate, zinc lactate, zinc formate, $ZnCl_2$, $ZnSO_4$, zinc acetate, zinc citrate, $Zn(NO_3)_2$, $Zn(CH_3SO_3)_2$ and zinc gallate, preferably $ZnCl_2$, $ZnSO_4$, zinc acetate, zinc citrate, $Zn(NO_3)_2$, $Zn(CH_3SO_3)_2$ and zinc gallate.

In another embodiment of the present invention, zinc salt is selected from ZnO, ZnO.aq, $Zn(OH)_2$ and $ZnCO_3$. Preference is given to ZnO.aq.

In one embodiment of the present invention, zinc salt is selected from zinc oxides with an average particle diameter (weight-average) in the range from 10 nm to 100 μm.

The cation in zinc salt can be present in complexed form, for example complexed with ammonia ligands or water ligands, and in particular be present in hydrated form. To simplify the notation, within the context of the present invention, ligands are generally omitted if they are water ligands.

Depending on how the pH of mixture according to the invention is adjusted, zinc salt can change. Thus, it is for example possible to use zinc acetate or $ZnCl_2$ for preparing formulation according to the invention, but this converts at a pH of 8 or 9 in an aqueous environment to ZnO, $Zn(OH)_2$ or ZnO.aq, which can be present in non-complexed or in complexed form.

Zinc salt may be present in those detergent compositions for cleaners according to the invention which are solid at room temperature are preferably present in the form of particles which have for example an average diameter (number-average) in the range from 10 nm to 100 μm, preferably 100 nm to 5 μm, determined for example by X-ray scattering.

Zinc salt may be present in those detergent compositions for home which are liquid at room temperature in dissolved or in solid or in colloidal form.

In one embodiment of the present invention, detergent compositions for cleaners and laundry detergent compositions comprise in total in the range from 0.05 to 0.4% by weight of zinc salt, based in each case on the solids content of the composition in question.

Here, the fraction of zinc salt is given as zinc or zinc ions. From this, it is possible to calculate the counterion fraction.

In one embodiment of the present invention, detergent compositions for cleaners and laundry detergent compositions according to the invention are free from heavy metals apart from zinc compounds. Within the context of the present, this may be understood as meaning that detergent compositions for cleaners and laundry detergent compositions according to the invention are free from those heavy metal compounds which do not act as bleach catalysts, in particular of compounds of iron and of bismuth. Within the context of the present invention, "free from" in connection with heavy metal compounds is to be understood as meaning that the content of heavy metal compounds which do not act as bleach catalysts is in sum in the range from 0 to 100 ppm, determined by the leach method and based on the solids content. Preferably, formulation according to the invention has, apart from zinc, a heavy metal content below 0.05 ppm, based on the solids content of the formulation in question. The fraction of zinc is thus not included.

Within the context of the present invention, "heavy metal" are deemed to be any metal with a specific density of at least 6 g/cm$^3$ with the exception of zinc. In particular, the heavy metals are metals such as bismuth, iron, copper, lead, tin, nickel, cadmium and chromium.

Preferably, detergent compositions for cleaners and laundry detergent compositions according to the invention comprise no measurable fractions of bismuth compounds, i.e. for example less than 1 ppm.

In one embodiment of the present invention, detergent compositions according to the present invention comprise one or more further ingredient such as fragrances, dyestuffs, organic solvents, buffers, disintegrants for tabs, and/or acids such as methanesulfonic acid.

Preferred example detergent compositions for automatic dishwashing may be selected according to table 1.

TABLE 1

Example detergent compositions for automatic dishwashing

| All amounts in g/sample | ADW.1 | ADW.2 | ADW.3 |
|---|---|---|---|
| racemic MGDA-Na$_{2.5}$H$_{0.5}$, with 4 ppm of Na$_2$SO$_4$ and 16 ppm NaCl | 30 | 22.5 | 15 |
| Protease | 2.5 | 2.5 | 2.5 |
| Amylase | 1 | 1 | 1 |
| n-C$_{18}$H$_{37}$—O(CH$_2$CH$_2$O)$_9$H | 5 | 5 | 5 |

TABLE 1-continued

Example detergent compositions for automatic dishwashing

| All amounts in g/sample | ADW.1 | ADW.2 | ADW.3 |
|---|---|---|---|
| Polyacrylic acid $M_w$ 4000 g/mol as sodium salt, completely neutralized | 10 | 10 | 10 |
| Sodium percarbonate | 10.5 | 10.5 | 10.5 |
| TAED | 4 | 4 | 4 |
| $Na_2Si_2O_5$ | 2 | 2 | 2 |
| $Na_2CO_3$ | 19.5 | 19.5 | 19.5 |
| Sodium citrate dihydrate | 15 | 22.5 | 30 |
| HEDP | 0.5 | 0.5 | 0.5 |
| ethoxylated polyethylenimine, 20 EO/NH group, $M_n$: 30,000 g/mol | option-ally: 0.1 | option-ally: 0.1 | option-ally: 0.1 |

Laundry detergent compositions according to the invention are useful for laundering any type of laundry, and any type of fibres. Fibres can be of natural or synthetic origin, or they can be mixtures of natural of natural and synthetic fibres. Examples of fibers of natural origin are cotton and wool. Examples for fibers of synthetic origin are polyurethane fibers such as Spandex® or Lycra®, polyester fibers, or polyamide fibers. Fibers may be single fibers or parts of textiles such as knitwear, wovens, or nonwovens.

In other embodiments, inventive mixtures may be applied in oilfield applications, for example in processes for recovering crude oil and/or gas from subterranean formations. Specific examples are processes of controlling iron, processes for acidizing, inhibition of scale formation, dissolution of scale already formed, and removal of oil filter cakes.

The term "recovering of crude oil and/or gas" shall include any processes which may be applied in course of recovering crude oil from subterranean formations starting with drilling wellbores into subterranean formations to processing crude oil and/or gas on the oilfield after producing it from a wellbore. Specifically, the term "recovering of crude oil and/or gas" shall include but be not limited to operations such as drilling of wellbores, completion of wellbores, such as cementing, stimulation such as fracturing and/or acidizing, enhanced oil recovery, conformance control, splitting crude oil—water emulsions, scale inhibition and/or removal of scale form oilfield equipment and/or subterranean formations, iron control, or corrosion protection of oilfield equipment.

In particular, inventive mixtures may be used as additives in fluids, in particular aqueous fluids to be used in the abovementioned oilfield operations. Depending on the intended use such fluids may comprise further components including but not limited to surfactants, polymers such as thickening polymers, bases, acids, or other additives, in particular acids. The concentration of inventive mixtures may range from 0.01% by weight to 30% by weight relating to the sum of all components of such aqueous fluid. In one embodiment 0.05% to 2% by weight, preferably 0.1 to 1% by weight of an inventive mixture is used while in other embodiments higher amounts may be used such as for, but not limited to 5% by weight to 30% by weight.

For making such aqueous fluids an inventive mixture or an aqueous solution containing such inventive mixture may be used and mixed with the fluid, preferably an aqueous and other components.

Examples of fluids to be used in oilfield operations include drilling fluids, completion fluids, spacer fluids, fracturing fluids, acidizing fluids, fluids for enhanced oil recovery, fluids for conformance control, fluids for iron control or scale removal fluids.

Some preferred oilfield applications are described below.

In one preferred embodiment of the present invention inventive mixtures are used in a process for acidizing subterranean formations, hereinafter also being referred to as inventive acidizing process.

In course of acidizing subterranean, oil and/or gas bearing formations acids dissolve the rock generating new pores, channels and the like in the formation and/or remove scales present in the formation and thereby increase the permeability of the formation.

In course of acidizing operations iron contaminations may cause problems because acidic formulations used may dissolve iron and/or iron compounds that are in contact with the acidic formulations. Examples comprise steel equipment such as wellbore tubing or iron containing minerals in the formation that are contacted by acidic formulation. Such dissolved iron may later, in particular with rising pH value due to the consumption of the acid used, form precipitates with organic or inorganic components—for instance as iron hydroxides. Such precipitates may plug the formation or at least hinder the flow of liquids in the formation. Adding a chelating agent that is able to complex iron (II) and iron (Ill) ion addresses said problem. Techniques of preventing the precipitation of iron compounds are also known as "iron control".

In one embodiment of the present invention subterranean formations are selected from formations comprising carbonates. Such subterranean formation may be a subterranean formation that predominantly comprises carbonates, in particular $CaCO_3$ and/or $MgCO_3$, for example in the form of magnesite, dolomite, limestone, chalk or aragonite. Further carbonates, such as, for example, $SrCO_3$ or $BaCO_3$, may be present in addition. Subterranean formations can also comprise impurities or can be mixed with other formations, for example silicate formations. In other embodiments, carbonates, in particular $CaCO_3$ and/or $MgCO_3$, may only be present in the respective formation in minor amounts, preferably in amorphous or poorly crystallized forms. Examples include silicate formations or shale formations comprising some amounts of carbonate, e.g. silicate formations in which silicate and/or quartz particles may be agglomerated by carbonate.

The temperature in subterranean formations may be from 20° C. to 250° C.

Methanesulfonic acid may advantageously be used for the treatment of carbonate-based rock formations having a temperature of at least 60° C., in particular from 60 to 250° C.

For carrying out the acidizing method according to the invention, an acidic aqueous formulation is injected into the subterranean formation through at least one wellbore at a pressure sufficient to penetrate into the subterranean formation.

When acidic aqueous formulation contacts acid-soluble components of a subterranean formation, for example a carbonate-based rock and/or carbonate impurities in a formation such component reacts with the acid and thereby increases the permeability of the subterranean formation. By way of example, the increased permeability may be caused by the dissolution of carbonate impurities clogging pores, cavities and the like in the formation, increasing existing channels, pores and the like and/or forming new channels, pores and the like. The increased permeability may result in a higher oil production when resuming the oil production after the acidizing treatment.

The penetration depth of the acidizing treatment may depend on such parameters as the injection rate, time of treatment but also on the nature of the aqueous formulation itself. When the acid injected is spent than it will have no longer an effect on the formation even if the formulation is forced to penetrate further into the formation.

Acidic aqueous formulation may be injected into a production well or into an injection well. A production well is a well through which mineral oil or natural gas is also withdrawn. An injection well serves for forcing in flooding media for maintaining the pressure in the deposit. A treatment of the injection well reduces pressure drops when the flooding medium is forced in and thus also advantageously contributes to higher productivity.

The acidizing treatment according to the invention can be a so called "matrix acidizing" process. In the case of matrix acidizing the pressure of injection is limited to pressures not sufficient to hydraulically create fissures and/or fractures in the formation.

The acidizing treatment according to the invention may be combined with a fracturing process (the so called "fracture acidizing"). In the case of fracture acidizing the pressure of injection is sufficient to hydraulically create fissures and/or fractures in the formation.

In a first embodiment of the acidizing process an aqueous formulation comprising at least water, an inventive mixture and an acid is used. Optionally, the aqueous formulation may comprise further components including but not limited to surfactants, diverting agents and/or corrosion inhibitors.

Examples of suitable acids are HCl, HF, organic acids, such as, for example, formic acid, acetic acid, p-toluenesulfonic acid amido sulfonic acid or alkanesulfonic acids. Preferred alkanesulfonic acids have the general formula $R^{12}$—$SO_3H$, where $R^{12}$ is a straight-chain, branched or cyclic alkyl radical. For example, $R^{12}$ is selected from straight-chain or branched $C_1$-$C_6$-alkyl, preferably $C_1$-$C_4$-alkyl. Most preferably, $R^{12}$ is methyl, that means the alkane sulfonic acid is methanesulfonic acid.

In special embodiments, a mixture of two or more acids may be used. Examples of suitable acid mixtures may be selected from mixtures of methanesulfonic acid and HF, methanesulfonic acid and HCl, formic acid and acetic acid, acetic acid and HCl, formic acid and HCl, and HF and HCl. Mixtures of HF and HCl are also known as mud acid any may be used for example in a weight ratio of 9:1 or 12:3.

Suitable acids may be selected in particular according to the nature of the formation to be acidized. By way of example, if the formation comprises silicates and it is desired to also dissolve such silicates HF or acid mixtures comprising HF should be used.

Methanesulfonic acid (abbreviated to MSA) is particularly preferably used. Methanesulfonic acid is a very strong acid ($pK_a$: −2) but has a significantly lower vapor pressure than HCl or formic acid. It is therefore very particularly suitable also for use at relatively high temperatures. Methanesulfonic acid can therefore advantageously be used for the treatment of subterranean formations having a temperature of at least 60° C., in particular from 60 to 250° C.

The concentration of acid in the aqueous solutions may be chosen in wide ranges.

By way of example, the concentration of methanesulfonic acid may be from 1% to 50% by weight with respect to all components of the aqueous solution, preferably from 5% to 50% by weight, more preferably 10% to 30% by weight, and even more preferably 15% to 25% by weight.

The concentration of HCl used may be from 2% to 28% by weight, preferably 2 to 20% by weight and even more preferably 5% to 15% by weight.

In addition to water and an acid, the aqueous formulation used may comprise small amounts of organic water-miscible solvents. These may be, in particular, alcohols, for example methanol, ethanol or propanol, however as a rule, the proportion of water is at least 80% by weight, preferably 90% by weight and particularly preferably at least 95% by weight, based in each case on the total amount of all solvents used.

The concentration of chelating agent in aqueous formulation may be in the range of from 0.05% to 2% by weight, preferably 0.1 to 1% by weight, relating to the total of all components of the respective aqueous formulation, or from 2.5% to 30% by weight with respect to the total formulation, preferably 5% to 25% by weight and for example 10% to 20% by weight.

The pH-value of the aqueous formulation in particular depends on the nature and amount of the acid used. It may be from zero to 5, for example from 0 to 2, or from 3 to 6.

Aqueous formulations inventive mixtures may additionally comprise one or more additives. Examples of such additives may be selected from polymers for increasing the viscosity, foam formers or foam breakers, oxidizing agents, enzymes, assistants for reducing the friction or for controlling paraffin precipitations and biocides or surfactants, and in particular retarding surfactants.

In addition inventive mixtures, one or more further complexing agents and/or their respective salts may be used, including but not limited to glutamic acid N,N-diacetic acid (GLDA), nitrilotriacetic acid (NTA), ethylenediaminetetraacetic acid (EDTA), diethylenetriaminepentaacetic acid (DTPA), or hydroxyethylethylenediaminetriacetic acid (HEDTA). The content of additional additives is chosen by the person skilled in the art according to the desired use.

In one embodiment of the present invention the aqueous formulation used comprises at least water, an acid, an inventive mixture and a corrosion inhibitor that is soluble in the acidic aqueous formulation.

Examples of suitable water-soluble corrosion inhibitors comprise alkyne derivatives, for example propargyl alcohol or 1,4-butynediol.

In a preferred embodiment of the invention, said derivatives are alkoxylated alkyne derivatives of the general formulae (XI) and (XII)

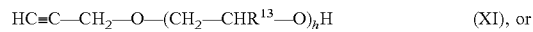

$$HC{\equiv}C-CH_2-O-(CH_2-CHR^{13}-O)_hH \quad (XI), or$$

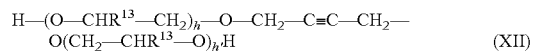

$$H-(O-CHR^{13}-CH_2)_{h'}-O-CH_2-C{\equiv}C-CH_2-O(CH_2-CHR^{13}-O)_hH \quad (XII)$$

wherein the radicals $R^{13}$, in each case independently of one another, are H or methyl and the indices h and h', independently of one another, are from 1 to 10.

Said values for h are thus average chain lengths, and the average value need not be a natural number but may also be any rational number. The variables h and h' are preferably numbers from 1 to 3. The alkylenoxy groups may be exclusively ethylene oxide units or exclusively propylene oxide units. However, they may be groups that have both ethylene oxide units and propylene oxide units. Polyoxyethylene units are preferred.

In a further embodiment of the present invention inventive aqueous formulations comprise water, an acid, an inventive mixture, and a surfactant. In a preferred embodiment, the formulation additionally comprises a corrosion inhibitor soluble in inventive acidic aqueous formulations.

Suitable surfactants may be selected from the group of anionic surfactants, cationic surfactants, non-ionic surfactants, amphoteric surfactants or zwitterionic surfactants. Mixtures of two or more surfactants may be selected as well. Examples of suitable surfactants comprise alk(en)ylpolyglucosides, alkylpolyalkoxylates, alkylphenolalkoxylates, sorbitan esters which may be alkoxylated, alkanolamides, amine oxides, alkoxylated fatty acids, alkoxylated fatty amines alkoxylated alkyl amines or quaternary ammonium compounds.

Surfactants may serve several functions in formulations for acidizing. In one embodiment, foaming surfactants may be used. Formulations for acidizing comprising such foaming surfactants may be foamed before or during injection into the subterranean formation. Foams of acidizing formulations have a higher viscosity than liquid formulations and therefore flow into subterranean formations more uniformly. Examples of suitable foaming surfactants comprise alkyl sulfates such as sodium lauryl sulfate, betaines such as alkylamidobetaines, amine oxides, or quaternary ammonium compounds such as trimethyl tallow ammonium salts.

In another embodiment, the surfactants are so-called retarding surfactants. If very reactive acids such as HCl are used for acidizing, such acid quickly reacts with the formation once it gets into contact with the formation and therefore the acid may quickly become spent in the near wellbore regions of the respective subterranean formation. Retarding surfactants slow down the reaction between the acid and the formation thereby allowing the acid to penetrate deeper into the formation. In one embodiment so-called "wormholes" may be formed. Examples of suitable retarding surfactants comprise sulfonates of the general formula $R^{14}SO_3M^3$, wherein $R^{14}$ is a $C_8$ to $C_{25}$ hydrocarbon moiety and $M^3$ is an alkali metal ion or an ammonium ion.

In another embodiment of the present invention an emulsion of an inventive aqueous acidic formulation in a non-polar organic solvent may be used. Examples of suitable non-polar organic solvents are hydrocarbons such as xylene or toluene or high boiling (e.g. having a boiling point of at least 160° C. at normal pressure) aromatic and/or aliphatic hydrocarbon fractions. Preferably, a surfactant for stabilizing the emulsion should be used. Such emulsions may also be used for retarding the action of the acid on the formation thereby allowing the acid to penetrate deeper into the formation.

In one embodiment the acidic aqueous formulation is specifically adapted for fracture acidizing and comprises at least water, the MGDA mixture described above, a proppant and thickening components such as thickening surfactants and/or thickening polymers. Proppants are preferably selected from small hard inorganic or organic particles, for instance sand particles. Proppants may be transported by the acidic aqueous formulation into newly formed fractures or fissions in order to keep them open after pressure has been released. Examples of thickening polymers comprise polyacrylamide or copolymers of acryl amide and other water-soluble monomers such as for instance acrylic acid.

Iron Control

In another preferred embodiment of the present invention the process the process in which inventive mixtures may be used is a process of controlling iron.

In the course of using acidic formulations in processes for recovering crude oil and/or gas from subterranean formations the formulations may contact steel equipment such as wellbore tubing, and iron and/or iron compounds that are in contact with the acidic formulation and or iron compounds in the formation or at the surfaces of equipment such as rust and the acidic formulation may be dissolved. Furthermore, used components of aqueous formulations such as for instance acids may comprise iron impurities. Such dissolved iron may later, in particular with rising pH value due to the consumption of acid, form precipitates with organic or inorganic components for instance as iron hydroxides thereby plugging the formation or at least hinder the flow of liquids in the formation and/or equipment.

Adding an inventive mixture addresses said problem. Inventive mixtures are able to complex iron (+II) ions and iron (+III) ions. Techniques of preventing the precipitation of iron compounds are also known as "iron control".

For iron control one or more inventive mixtures may be added to aqueous formulations for oilfield uses.

The amount of inventive mixtures in such aqueous formulations may be from 0.05% to 2% by weight, preferably 0.1 to 1% by weight, relating to the total of all components of the aqueous formulation.

Scale Inhibition and/or Dissolution of Scale

Another preferred embodiment of the invention the process wherein inventive mixtures may be used refers to a process for the inhibition and/or dissolution of scale. Components for the inhibition and/or dissolution of scale are often simply termed as "scale inhibitors".

In the course of mineral oil and/or natural gas production, solid deposits of inorganic or organic substances can form in a mineral oil and/or natural gas containing subterranean formation itself, in underground installation parts, for example the well lined with metal tubes, and in aboveground installation parts, for example separators. The formation of such solid deposits is extremely undesirable because they can at least hinder the production of mineral oil or natural gas and, in extreme cases, lead to complete blockage of the installation parts affected. Such deposited scales typically comprise carbonates such as calcium carbonate or magnesium carbonate but also sulfates, such as calcium sulfate, strontium sulfate or barium sulfate.

Such scales may be dissolved using suitable aqueous formulations comprising water and an inventive mixture. In one embodiment an aqueous formulations comprising water and an inventive mixture may be used.

The concentration of inventive mixture in suitable aqueous formulations may be in the range of from 0.5% to 10% by weight, preferably 1 to 3% by weight, relating to the total respective aqueous formulation.

Aqueous formulations for scale inhibition may optionally comprise further components, in particular acids and/or additional scale inhibitors, so-called co-inhibitors.

Examples of acids are HCl and in particular methanesulfonic acid.

Examples of co-inhibitors are complexing agents other than MGDA and GLDA and/or their respective salts, including but not limited to ethylenediaminetetraacetic acid (EDTA), diethylenetriaminepentaacetic acid (DTPA), and hydroxyethylethylenediaminetriacetic acid (HEDTA). Further examples of co-inhibitors are polyacrylic acid or copolymers comprising acrylic acid or salts thereof, phosphate or phosphonate groups containing compounds such as alkylphenolphosphate ester acids, hydroxy-amino phosphates esters, polymers comprising phosphate or phosphonate groups.

By way of example, the weight ratio of inventive mixture to co-inhibitor may be in the range of from 10:1 to 1:10.

For performing the process of scale inhibition a surface with deposited scales is brought into contact with an aqueous formulation described above, for example by rinsing installations with the aqueous formulation.

Use of Inventive Mixtures for the Removal of Filter Cakes

In another preferred embodiment of the present invention, inventive mixtures are used in a process of removing filter cakes.

In oil well operations filter cakes may be formed within a subterranean formation by the introduction of a material capable of forming an impermeable layer on the walls of the wellbore, in particular during the drilling. Such a filter cake prevents the flow of drilling fluid into the formation. Let aside the loss of drilling fluid, drilling fluid in the formation may damage the near wellbore area and thereby hinder the flow of oil or gas from the formation into the wellbore. For this reason such a filter cake has to be removed.

For the process of removing filter cakes according to the present invention suitable aqueous formulations comprising at least water and an inventive mixture are used. In one embodiment an aqueous formulations comprising at least water and inventive mixture above may be used.

The concentration of inventive mixture may be from 0.1% to 40% by weight, preferably 5 to 20% by weight, relating to the total aqueous formulation.

Suitable formulations for removing filter cakes optionally comprise one or more further components such as those disclosed in U.S. Pat. No. 6,494,263 B2.

For removing filter cakes the respective filter cake is brought into contact with the aqueous formulation described by injecting the aqueous formulation into the wellbore.

Use of Inventive Mixtures for Enhanced Oil Recovery

In another preferred embodiment of the present invention the process in which inventive mixtures may be used is a process of enhanced oil recovery, preferably a process of alkali-surfactant flooding or alkali-surfactant-polymer flooding, the latter one also known as "ASP flooding".

In enhanced oil recovery operations an aqueous formulation comprising a base and at least one surfactant and/or a thickening agent, said thickening agent being selected from water-soluble polymers, is injected into a mineral oil deposit through at least one injection well. Then, crude oil is withdrawn from the deposit through at least one production well. Water-soluble polymers and/or surfactants mobilize oil which otherwise remained caught in the subterranean formation.

Crude oil usually comprises one or more naturally occurring acids such as naphthenic acid(s). Adding bases to aqueous formulations for enhanced oil recovery, i.e. using aqueous fluids having a pH value of more than 7, preferably 9 to 13, results—after injection into the formation—in a conversion of said naturally occurring acids into the respective salts. Such salts of naphthenic acids have surface-active properties and support the process of mobilizing oil.

Besides crude oil subterranean oil bearing formations comprise formation water that usually comprises salts, including but not limited to salts of bivalent ions such as $Ca^{2+}$ or $Mg^{2+}$. Often formation water is also used as fluid for making the aqueous formulations for enhanced oil recovery. If said $Ca^{2+}$ and/or $Mg^{2+}$ ions come into contact with bases hydroxides may precipitate and plug the formation.

For the process of enhanced oil recovery according to the present invention an aqueous solution is used which comprises water, a base, a surfactant and an inventive mixture. The concentration of inventive mixtures in such aqueous solutions may be from 0.1% to 40% by weight, preferably 0.2 to 20% by weight, for example 0.5 to 2% by weight relating to the respective aqueous solution.

The water to be used for such aqueous solution may be fresh water, sea water, brine or formation water or mixtures thereof.

In principle, it is possible to use any kind of base with which the desired pH can be attained. Examples of particularly suitable bases include alkali metal hydroxides, for example NaOH or KOH, or alkali metal carbonates, for example $Na_2CO_3$.

The pH of said aqueous solutions may be at least 8, preferably at least 9, especially 9 to 13, even more preferably 10 to 12 and, for example, 10 to 11.

Examples of suitable surfactants for alkali-surfactant flooding and for ASP flooding include surfactants comprising sulfate groups, sulfonate groups, polyoxyalkylene groups, anionically modified polyoxyalkylene groups, betaine groups, glucoside groups or amine oxide groups, for example alkylbenzenesulfonates, olefinsulfonates, amidopropyl betaines, alkyl polyglucosides, alkyl polyalkoxylates or alkyl polyalkoxysulfates, -sulfonates or -carboxylates. It is possible with preference to use anionic surfactants, optionally in combination with nonionic surfactants. The total concentration of surfactants is generally 0.01% by weight to 2% by weight, preferably 0.05 to 1% by weight and, for example, 0.1 to 0.8% by weight, based on the total respective aqueous solution.

Optionally, the solution used may comprise at least one water-soluble polymer that may be used as thickener. Thickeners may be selected from high molecular weight polyacrylamides or copolymers of acryl amide such as acrylamide-acrylic acid copolymers. Usually, such thickeners have a weight average molecular weight $M_w$ of at least 500,000 g/mol, preferably 1 to 30 Mio g/mol.

Optionally, the aqueous formulations may of course comprise one or more further components. Examples of further components include biocides, stabilizers, free-radical scavengers, inhibitors or cosolvents.

For performing the process of enhanced oil recovery a solution described above is injected into a mineral oil deposit through at least one injection well and crude oil is withdrawn from the deposit through at least one production well.

The invention is further illustrated by working examples.

General Remarks:

Percentages refer to mole-% unless expressly noted otherwise. The percentage of (A) was determined by HPLC analysis, and the sum of (A) to (B) by determination of the iron binding capacity.

Example 1:

Compound (I a): L-$CH_3$—$CH(COOX^2)$—$N(CH_2CN)_2$ with $X^2$ is $(Na_yH_{1-y})$, y is 0.65. Compound (I a) was made according to WO 2015/036324.

Step (a.1): an amount of 293.3 g (31.6 wt.-%, 0.51 mol) of compound (I a) was used as aqueous solution.

Step (b.1): a 1-l-three-necked flask was charged with 100 g of 10% by weight aqueous solution of NaOH (corresponds to 0.25 mol NaOH). Under stirring, the solution from step (a.1) and 59.6 g of 50% by weight aqueous NaOH (0.745 mol) were added simultaneously over a period of 120 minutes under cooling. The temperature did not exceed 40° C. The reaction mixture was stirred additional 60 minutes at 40° C.

Step (c.1): the reaction mixture obtained from step (b.1) was stirred at 70° C. for 60 minutes, sub-step (c2.1).

Then, the reaction mixture was refluxed for 240 minutes at a reduced pressure of 900 to 950 mbar, the temperature rose up to 90 to 100° C., sub-step (c3.1). Since considerable amounts of ammonia evaporated together with water, the loss of water was partially compensated by adding deionized water. It was observed that the temperature dropped to lower temperatures.

After completion of sub-step (c3.1), an orange-brown reaction mixture of 362.2 g inventive mixture (IM.1) was obtained. (IM.1) displayed an iron-binding capacity of 1.513 mmol/g. This corresponds to a yield of 97% (calculated as MGDA-$H_3$). The NTA content (calculated as NTA-$H_3$) was <0.1 wt.-% according to HPLC analysis.

The ratio of components (A) to (B) was 1.4 to 1. The pH value was 10.2.

The content of NaCl was 16.6 mg/kg, and the content of $Na_2SO_4$ was about 4.4 mg/kg, both determined by ICP measurements.

The invention claimed is:

1. A process for making a chelating agent comprising:
   (A) a compound according to formula (I):

$$R^1\text{—CH}(COOX^1)\text{—N}(CH_2COOX^1)_2 \quad (I)$$

(B) at least one compound having a formula selected from the group consisting of formulae (III a) and (III b):

$$R^1\text{—CH}(COOX^1)\text{—N}(CH_2COOX^1)(CH_2CONH_2) \quad (III\ a)$$

$$R^1\text{—CH}(COOX^1)\text{—N}(CH_2CONH_2)_2 \quad (III\ b);\ and$$

in total 1 ppm to 1.5% by weight of an inorganic non-basic salt based on a total amount of components (A) and (B),
   wherein:
   $R^1$ is selected from the group consisting of $C_1$-$C_4$ linear alkyl, $C_1$-$C_4$ branched alkyl, phenyl, benzyl, $CH_2OH$, and $CH_2CH_2COOX^1$,
   $X^1$ is $(Na_xH_{1-x})$,
   x is in a range of from 0.6 to 1, and
   wherein component (A) and component (B) are present in a molar ratio in a range of from 2:1 to 0.1:1,
   the process comprising:
   (a) contacting a solid, a slurry or a solution of a compound according to formula (II)

$$R^1\text{—CH}(COOX^2)\text{—N}(CH_2CN)_2 \quad (II)$$

wherein:
   $X^2$ is $(Na_yH_{1-y})$,
   y is in the range of from zero to 1,
   with an aqueous solution of sodium metal hydroxide, wherein a molar ratio of sodium metal ions to nitrile groups is in a range of from 0.6:1 to 0.95:1, and
   (b) reacting the compound according to formula (II) with the sodium metal hydroxide.

2. The process according to claim 1 wherein the reacting is performed at a temperature in a range of from 30 to 200° C.

3. The process according to claim 1, wherein x is in a range of from 0.7 to 0.85.

4. The process according to claim 1, wherein $R^1$ in formula (II) is methyl, and compound (II) is predominantly an L-enantiomer, the ratio of L to D being in a range of from 95:1 to 100:1.

5. The process according to claim 1, wherein the reacting comprises at least two stages (c1) and (c2), wherein stage (c2) is performed at a temperature at least 20° C. higher than stage (c1).

6. A mixture of compounds, comprising
   (A) at least one compound according to formula (I):

$$R^1\text{—CH}(COOX^1)\text{—N}(CH_2COOX^1)_2 \quad (I)$$

(B) at least one compound having a formula selected from the group consisting of formulae (III a) and (III b):

$$R^1\text{—CH}(COOX^1)\text{—N}(CH_2COOX^1)(CH_2CONH_2) \quad (III\ a)$$

$$R^1\text{—CH}(COOX^1)\text{—N}(CH_2CONH_2)_2 \quad (III\ b);\ and$$

in total 1 ppm to 1.5% by weight of an inorganic non-basic salt,
   wherein:
   $R^1$ is selected from the group consisting of $C_1$-$C_4$ linear alkyl, $C_1$-$C_4$ branched alkyl, phenyl, benzyl, $CH_2OH$, and $CH_2CH_2COOX^1$,
   $X^1$ is $(Na_xH_{1-x})$,
   x is in a range of from 0.6 to 1, and
   wherein component (A) and component (B) are present in a molar ratio in a range of from 2:1 to 0.1:1.

7. The mixture according to claim 6, wherein $R^1$ is methyl.

8. The mixture according to claim 6, wherein compound (I) is a racemic mixture.

9. The mixture according to claim 6, wherein component (A) is a mixture of enantiomers comprising predominantly a respective L-enantiomer with an enantiomeric excess (ee) in a range of from 10 to 98%.

10. An aqueous solution comprising the mixture according to claim 6.

11. A method of removing alkali earth metal cations and/or iron cations from water, comprising contacting the mixture according to claim 6 with water.

12. A detergent composition comprising the mixture according to claim 6.

13. The detergent composition of claim 12, which is suitable for automatic dishwashing.

\* \* \* \* \*

UNITED STATES PATENT AND TRADEMARK OFFICE
CERTIFICATE OF CORRECTION

PATENT NO.        : 10,519,097 B2
APPLICATION NO.   : 15/573155
DATED             : December 31, 2019
INVENTOR(S)       : Armin Stamm et al.

Page 1 of 1

It is certified that error appears in the above-identified patent and that said Letters Patent is hereby corrected as shown below:

On the Title Page

Column 2, item (74), Line 2, "Neustdt," should read -- Neustadt, --.

Column 2, item (57), Line 2, "N(CH2COOX$^1$)$_2$" should read -- N(CH$_2$COOX$^1$)$_2$ --.

Column 2, item (57), Line 4, "(M$_\chi$H$_{1-\chi}$)," should read -- (M$_x$H$_{1-x}$), --.

In the Specification

Column 11, Line 29, "C1-C$_{10}$-alkyl" should read -- C$_1$-C$_{10}$-alkyl --.

Column 12, Line 51, "cocamidylpropyl" should read -- cocamidopropyl --.

Column 13, Line 38, "rutheniumor" should read -- ruthenium- or --.

Column 15, Line 44, "g/I" should read -- g/l --.

Column 18, Line 22, "(Ill)" should read -- (III) --.

Column 21, Line 61, "and or" should read -- and/or --.

In the Claims

Column 25, Line 13, Claim 1, "(I)" should read -- (I); --.

Column 25, Line 45, Claim 2, "claim 1" should read -- claim 1, --.

Signed and Sealed this
Third Day of November, 2020

Andrei Iancu
*Director of the United States Patent and Trademark Office*